United States Patent
Tsuzuki

(10) Patent No.: US 7,723,122 B2
(45) Date of Patent: *May 25, 2010

(54) METHOD FOR ANALYZING TEST SUBSTANCE BY SURFACE PLASMON RESONANCE ANALYSIS

(75) Inventor: Hirohiko Tsuzuki, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 1069 days.

This patent is subject to a terminal disclaimer.

(21) Appl. No.: 11/213,716

(22) Filed: Aug. 30, 2005

(65) Prior Publication Data

US 2006/0046306 A1 Mar. 2, 2006

(30) Foreign Application Priority Data

Aug. 31, 2004 (JP) ............................. 2004-251380

(51) Int. Cl.
*G01N 24/00* (2006.01)
*G01N 21/62* (2006.01)
*G01N 33/53* (2006.01)

(52) U.S. Cl. .................. 436/173; 436/171; 436/805
(58) Field of Classification Search .................. None
See application file for complete search history.

(56) References Cited

U.S. PATENT DOCUMENTS

| 5,047,213 | A | * | 9/1991 | Finlan et al. | ............. | 422/82.11 |
| 5,313,264 | A | * | 5/1994 | Ivarsson et al. | ............... | 356/73 |
| 6,093,536 | A | | 7/2000 | Drake et al. | | |
| 7,413,911 | B2 | * | 8/2008 | Ohtsuka | ...................... | 436/525 |
| 2006/0040326 | A1 | * | 2/2006 | Ohtsuka | ...................... | 435/7.1 |

(Continued)

FOREIGN PATENT DOCUMENTS

JP 07-174693 7/1995

(Continued)

OTHER PUBLICATIONS

Myszka, David G.; He, Xiaoyi; Dembo, Micah; Morton, Thomas A.; and Goldstein, Byron. "Extending the Range of Rate Constants Available from BIACORE: Interpreting Mass Transport-Infuenced Binding Date," Biophysical Journal, vol. 75, Aug. 1998, pp. 583-594.*

(Continued)

*Primary Examiner*—Jill Warden
*Assistant Examiner*—Bryan T Kilpatrick
(74) *Attorney, Agent, or Firm*—Sughrue Mion, PLLC

(57) ABSTRACT

It is an object of the present invention to provide a method for analyzing the interaction of a test substance with a ligand by analyzing a phenomenon whereby multiple test substances are simultaneously adsorbed to a ligand. The present invention provides a method for analyzing the interaction of test substances with a ligand by measuring the change in the surface plasmon resonance using a surface plasmon resonance measurement device wherein the above-described method comprises: supplying a solution containing two or more types of test substances after supplying a solution containing no test substances; measuring the change in the surface plasmon resonance; and analyzing the difference between the change in the surface plasmon resonance that is predicted from the adsorption rate constant (ka) and dissociation rate constant (kd) of each of the test substances that had previously been measured and the change in the surface plasmon resonance that has actually been measured.

5 Claims, 2 Drawing Sheets

U.S. PATENT DOCUMENTS

2007/0031893 A1* 2/2007 Some .................. 435/7.1

FOREIGN PATENT DOCUMENTS

| JP | 7-111435      | 11/1995 |
|----|---------------|---------|
| JP | 2001-324445   | 11/2001 |
| JP | 2001-330560 A | 11/2001 |
| JP | 2002-525631   | 8/2002  |
| JP | 2002-296177 A | 10/2002 |
| JP | 2002-310904   | 10/2002 |
| JP | 2002-335972   | 11/2002 |
| JP | 2003-502668   | 1/2003  |
| JP | 2003-302399   | 10/2003 |
| JP | 2005-513496   | 5/2005  |
| JP | 2006-507504   | 3/2006  |
| JP | 2006-511791   | 4/2006  |

OTHER PUBLICATIONS

Katsamba, Phinikoula S.; Park, Sungmin, and Laird-Offringa Ite A. "Kinetic studies of RNA-protein interactions using surface plasmon resonance," Methods, vol. 26, 2002, pp. 95-104.*

Müller, Kristian et al., Analytical Biochemistry 261, 149-158 (1998) "Model and Simulation of Multivalent Binding to Fixed Ligands".

Miura Norio, et al. Regenerable Surface Plasmon Resonance(SPR)-based Immunosensor for Highly Sensitive Measurement of Sub-ppb Levels of Benzo(a)pyrene. Chemistry Letters 2002(3), 342.

Butala H.D., "Journal of Colloid and Interface Science", Jul. 15, 2003. vol. 263, No. 2 pp. 420-431.

* cited by examiner

METHOD FOR ANALYZING TEST SUBSTANCE BY SURFACE PLASMON RESONANCE ANALYSIS

TECHNICAL FIELD

The present invention relates to a method for analyzing a test substance by surface plasmon resonance analysis.

BACKGROUND ART

In many cases, a compound used as a medicament interacts with a protein in a living body so as to exert its functions. For example, an enzyme inhibitor may bind to a target enzyme so as to inhibit the enzyme reaction, thereby changing biochemical reactions in a living body and expressing its pharmacological action. Thus, in order to search for a medicament, it is important to understand the binding strength of a protein with a candidate compound for such a medicament.

In recent years, as a means for analyzing the interactions of proteins with chemical substances, a surface plasmon resonance method has become a focus of attention. This method comprises immobilizing a protein on a metal surface such as gold, adding a chemical substance to the metal surface, and measuring the change in the surface plasmon resonance, so as to quantify the interaction of the protein with the chemical substance.

A test substance that is a chemical substance is adsorbed to a molecule interacting therewith (that is, a protein or the like immobilized on a metal surface) over time. The amount of the test substance adsorbed, that is, the change in SPR signals, is changed according to the following formula (1):

$$dR/dt = ka \cdot Cs \cdot (Rmax - R) - kd \cdot R \qquad \text{Formula (1)}$$

wherein, in the formula (1), R represents an SPR signal; Rmax represents the maximum SPR signal; ka represents an adsorption rate constant; kd represents a dissociation rate constant; and Cs represents a concentration of a test substance located adjacent to the metal surface.

Herein, the value of Cs is constant under ideal conditions where the liquid on the metal surface is constantly substituted with a fresh liquid. Thus, it is possible to determine ka and kd from the measurement results by solving a simple differential equation. A binding constant (KD) indicates the ratio between adsorption and dissociation, and it is represented by kd/ka.

Regarding such surface adsorption, when the n types of multiple compounds are adsorbed to a single adsorption site, the structure of which is not changed by adsorption, since such compounds are competitively adsorbed thereto, a change in SPR signals is represented by the following formula:

$$\frac{dR}{dt} = A \cdot \sum_{i=1}^{n} \left( Ka_i \cdot Cs_i \cdot \left(1 - \sum_{i=1}^{n} \theta_i\right) - kd_i \cdot \theta_i \right) \cdot MW_i \qquad \text{Formula (2)}$$

wherein, in the formula (2), A represents a constant used for conversion from the adsorbed weight to SPR signals; and $MW_i$, $Cs_i$, $\theta_i$, $ka_i$, and $kd_i$ represent the molecular weight of compound i, the concentration thereof, the adsorption site share thereof, an adsorption rate constant, and a dissociation rate constant, respectively.

Herein, if ka and kd have previously been known, a change in SPR signals obtained when the n types of multiple compounds are adsorbed can be calculated by formula (2).

In such surface absorption, a change in SPR signals obtained when the n types of multiple compounds are adsorbed to different adsorption sites is represented by the following formula (3):

$$\frac{dR}{dt} = \sum_{i=1}^{n} \left( Ka_i \cdot Cs_i \cdot \left(R\max_i - \sum_{i=1}^{n} R_i\right) - kd_i \cdot R_i \right) \qquad \text{Formula (3)}$$

wherein, in the formula (3), $R_i$ represents a change in SPR signals of compound i; and $Rmax_i$ represents the maximum adsorbed SPR signals of compound i.

Herein, if ka and kd have previously been known, a change in SPR signals obtained when the n types of multiple compounds are adsorbed can be calculated by formula (3).

It has been known that many physiologically active substances that become targets of medicaments change their structures when these substances bind to certain substances, so that they come to bind to other substances. For example, a single-stranded DNA forms a double strand together with DNA complementary thereto, so that it comes to bind to a certain type of DNA-recognition protein. In addition, it has also been known that a medicament acting on a certain type of enzyme (for example, cytokine, hormone, etc.) binds to a site of the enzyme known as an allosteric site that is different from a substrate recognition site, so that it changes the bindability of the substrate recognition site. Moreover, when a single protein constituting a complex protein is used by itself, it does not have the ability to recognize a physiologically active substance. However, when a plurality of such proteins form a complex, the complex protein can recognize a physiologically active substance.

Thus, for the development of medicaments, it is important to understand a phenomenon whereby multiple substances are simultaneously adsorbed to a ligand and to analyze a test substance by a means for evaluating such adsorption properties. However, the conventional adsorption analysis method only enables determination by competitive adsorption. For example, JP Patent Publication (Kokoku) No. 7-111435 B (1995) describes the analysis of multiple compounds to be analyzed binding to a sensor surface. Chem. Lett. 2002(3), 342 describes that a molecule to be analyzed is allowed to competitively bind to the surface, that it is compared with a case where no molecules to be analyzed are present, and that the concentration of the molecule to be analyzed is detected based on the fact that the change in SPR signals decreases as the above concentration decreases.

In order to search for medicaments, screening involving 1,000,000 or more types of compounds has commonly been conducted. It has been obvious that more experiments are required for the analysis of complex actions. Nevertheless, there have been no methods for differentiating competitive adsorption from a change in an adsorption site itself, so as to process a large amount of data rapidly. Accordingly, it is impossible to exhaustively study such complex actions under current circumstances.

DISCLOSURE OF THE INVENTION

It is an object of the present invention to provide a method for analyzing the interaction of a test substance with a ligand by analyzing a phenomenon whereby multiple test substances are simultaneously adsorbed to a ligand. It is another object of the present invention to provide a method for rapidly screening large quantities of test substances by differentiating the competitive adsorption of test substances to a ligand from the change in the adsorption site due to adsorption of such test substances to such a ligand.

As a result of intensive studies directed towards achieving the aforementioned objects, the present inventors have found the following fact. When a liquid in a flow channel system of a surface plasmon resonance measurement device is exchanged with a fresh liquid and the change in the surface plasmon resonance is measured, so as to analyze the interaction of a test substance with a ligand, a solution containing no test substances is first supplied, and a solution containing two or more types of test substances is then supplied. Thus, the change in the surface plasmon resonance is measured. By analyzing the difference between the change in the surface plasmon resonance that is predicted from the adsorption rate constant (ka) and dissociation rate constant (kd) of each of the test substances that had previously been measured and the change in the surface plasmon resonance that has actually been measured as described above, the change in the absorption site due to adsorption of the test substances to a ligand can be identified. The present invention has been completed based on these findings.

That is to say, the present invention provides: a method for analyzing the interaction of test substances with a ligand by measuring the change in the surface plasmon resonance using a surface plasmon resonance measurement device which comprises a metal film, a light source for generating a light beam, an optical system for allowing such a light beam to enter the interface of the metal film so that total reflection conditions can be obtained at the interface thereof and so that various incidence angles can be included, a flow channel system comprising a cell formed on the above metal film, and a light-detecting means for detecting the state of surface plasmon resonance by measuring the intensity of the light beam totally reflected at the above interface;

wherein the above-described method comprises: supplying a solution containing two or more types of test substances after supplying a solution containing no test substances; measuring the change in the surface plasmon resonance; and analyzing the difference between the change in the surface plasmon resonance that is predicted from the adsorption rate constant (ka) and dissociation rate constant (kd) of each of the test substances that had previously been measured and the change in the surface plasmon resonance that has actually been measured.

Preferably, the analysis method of the present invention comprises displaying the difference between the change in the surface plasmon resonance that is predicted from the adsorption rate constant (ka) and dissociation rate constant (kd) of each of the test substances that had previously been measured and the change in the surface plasmon resonance that has actually been measured, in the form of data.

Preferably, the change in the surface plasmon resonance can be measured in a state where the flow of the liquid has then been terminated after the liquid in the above-described flow channel system has been exchanged so that a solution containing no test substances is replaced with a solution containing two or more types of test substances.

Preferably, the difference between the change in the surface plasmon resonance that is predicted from the adsorption rate constant (ka) and dissociation rate constant (kd) of each of the test substances that had previously been measured and the change in the surface plasmon resonance that has actually been measured as described above is analyzed, and a test substance causing the change in the binding site due to the binding of the test substance to a ligand can be identified based on the presence of the above-mentioned difference.

BEST MODE FOR CARRYING OUT THE INVENTION

Figure 1:
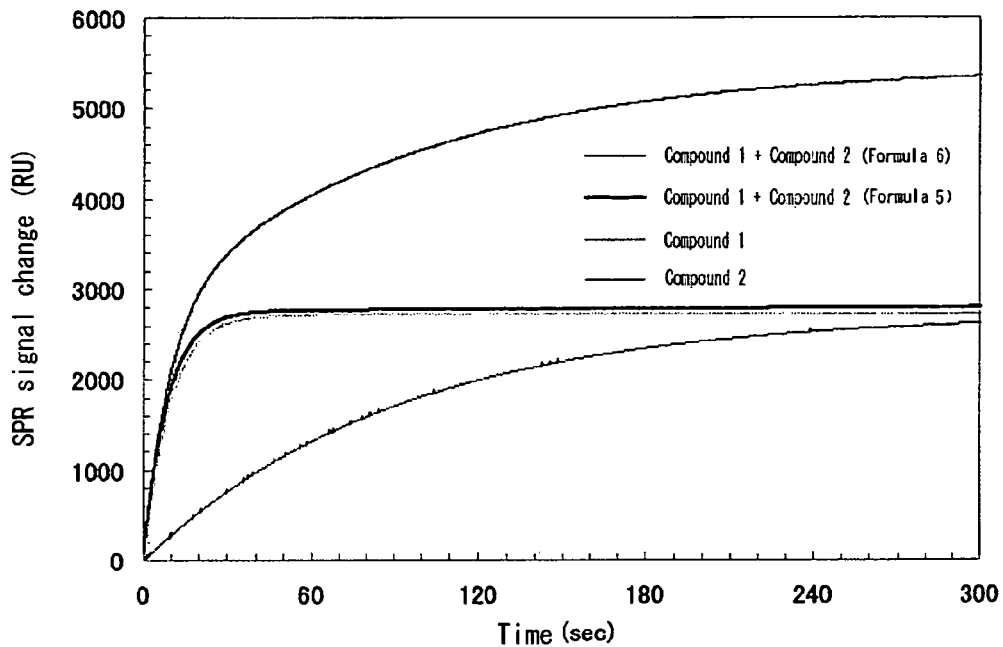
FIG. 1 shows the results obtained by calculating, according to the finite-difference method, a change in SPR signals obtained when compound 1 ($ka=1\times10^6$ $M^{-1} \cdot s^{-1}$, $kd=1\times10^{-2}$ $s^{-1}$) and compound 2 ($ka=1\times10^5$ $M^{-1} \cdot s^{-1}$, $kd=1\times10^{-3}$ $s^{-1}$), both having the same molecular weight, are supplied in the forms of a single solution and a mixed solution, each having a concentration of $1\times10^{-7}$ M, onto a gold modified surface with Rmax=3,000 RU under laminar flow conditions of a high linear velocity which achieves a constant compound concentration.

The embodiments of the present invention will be described below.

In the analysis method of the present invention, the change in the surface plasmon resonance is measured using a surface plasmon resonance measurement device, which comprises a metal film, a light source for generating a light beam, an optical system for allowing such a light beam to enter the interface of the metal film so that total reflection conditions can be obtained at the interface thereof and so that various incidence angles can be included, a flow channel system comprising a cell formed on the above metal film, and a light-detecting means for detecting the state of surface plasmon resonance by measuring the intensity of the light beam totally reflected at the above interface. The analysis method of the present invention is characterized in that it comprises, during the aforementioned measurement, supplying a solution containing two or more types of test substances after supplying a solution containing no test substances; measuring the change in the surface plasmon resonance; and analyzing the difference between the change in the surface plasmon resonance that is predicted from the adsorption rate constant (ka) and dissociation rate constant (kd) of each of the test substances that had previously been measured and the change in the surface plasmon resonance that has actually been measured.

The type of a test substance used in the present invention is not particularly limited, as long as it is a substance interacting with a physiologically active substance (ligand) described later in the present specification. Examples of such a test substance may include a low molecular weight organic compound, a high molecular weight compound, a nucleic acid such as DNA, a protein (including an antibody or the like), a peptide or a fragment thereof, sugar, and an amino acid.

In the present invention, when there is a difference between the change in the surface plasmon resonance that is predicted from the adsorption rate constant (ka) and dissociation rate constant (kd) of each of the test substances that had previously been measured and the change in the surface plasmon resonance that has actually been measured, it can be determined that there is a possibility that an adsorption site itself has changed due to adsorption of a substance to a ligand.

In the present invention, it is necessary for the adsorption rate constant (ka) and dissociation rate constant (kd) of each of the test substances to have been measured in advance. The adsorption rate constant (ka) and dissociation rate constant (kd) of a test substance can be obtained from a change in signal R at time t obtained in an experiment. For example, under laminar flow conditions of a constant compound concentration and a high linear velocity, such values can be obtained by non-linear regression analysis using the following formula (4):

$$dR/dt = ka \cdot Cs \cdot (Rmax - R) - kd \cdot R \quad \text{Formula (4)}$$

Herein, in order to reflect the binding state of a molecule to be analyzed to the metal surface, it is preferable that Rmax be obtained at the same time as the measurement of ka and kd. Thus, non-linear regression analysis with three unknowns is conducted.

When the test substances are adsorbed to a single site of a ligand, the change in the surface plasmon resonance predicted from the adsorption rate constant (ka) and dissociation rate constant (kd) of each of the test substances that had previously been measured as stated above can be calculated according to formula (5) described below. When the test substances are adsorbed to different adsorption sites thereof, such the change in the surface plasmon resonance can be calculated according to formula (6) described below. In addition, when the two above cases are mixed, such the change in the surface plasmon resonance can be calculated by the combined use of formula (5) with formula (6).

$$\frac{dR}{dt} = A \cdot \sum_{i=1}^{n} \left( Ka_i \cdot Cs_i \cdot \left(1 - \sum_{i=1}^{n} \theta_i\right) - kd_i \cdot \theta_i \right) \cdot MW_i \quad \text{Formula (5)}$$

$$\frac{dR}{dt} = \sum_{i=1}^{n} \left( Ka_i \cdot Cs_i \cdot \left(Rmax_i - \sum_{i=1}^{n} R_i\right) - kd_i \cdot R_i \right) \quad \text{Formula (6)}$$

wherein A represents a constant used for conversion from the adsorbed weight to SPR signals; $MW_i$, $Cs_i$, $\theta_i$, $ka_i$, and $kd_i$ represent the molecular weight of compound i, the concentration thereof, the adsorption site share thereof, an adsorption rate constant, and a dissociation rate constant, respectively; $R_i$ represents a change in SPR signals of compound i; and $Rmax_i$ represents the maximum adsorbed SPR signals of compound i.

Any calculation methods can be applied herein. Examples of such calculation methods may include: a method, which comprises first obtaining an analytical solution and then calculating an SPR signal at each instance of measurement; and a method of calculating the amount of a change in SPR signals at minute intervals according to the finite-difference method.

FIG. 1 shows the results obtained by calculating, according to the finite-difference method using the above formulas (5) and (6), a change in SPR signals obtained when compound 1 (ka=1×10$^6$ M$^{-1}$·s$^{-1}$, kd=1×10$^{-2}$ s$^{-1}$) and compound 2 (ka=1× 10$^5$ M$^{-1}$·s$^{-1}$, kd=1×10$^{-3}$ s$^{-1}$), both having the same molecular weight, are supplied in the forms of a single solution and a mixed solution, each having a concentration of 1×10$^{-7}$ M, onto a gold modified surface with Rmax=3,000 RU under laminar flow conditions of a constant compound concentration and a high linear velocity. As is clear from FIG. 1, formula (6) constitutes a simple sum of single signals, but formula (5) does not constitute such a simple sum of single signals.

In the present invention, it is preferable to display the difference between the change in the actually measured signals and the change in the surface plasmon resonance calculated from the adsorption rate constant (ka) and dissociation rate constant (kd) of each of the compounds that had previously been measured while the change in the surface plasmon resonance generated due to adsorption of two or more types of multiple test substances is measured, or after such measurement. Any display methods can be applied herein. Examples of such display methods may include a method of displaying a difference in a binding curve and a method of simply displaying only a degree of derivation.

In an embodiment of the present invention, the change in the surface plasmon resonance can be measured in a state where a liquid in a flow channel system of a surface plasmon resonance measurement device has been exchanged so that a solution containing no test substances is replaced with a solution containing two or more types of test substances and where the flow of the liquid has then been terminated. By such measurement, the noise width of a change in signals of a reference cell during the measurement time and baseline fluctuation can be suppressed, thereby obtaining binding detection data with high reliability. The time required for termination of the flow of the liquid is not particularly limited. For example, it is between 1 second and 30 minutes, preferably between 10 seconds and 20 minutes, and more preferably between 1 minute and 20 minutes.

In the present invention, preferably, a reference cell, to which a substance interacting with a test substance does not bind, is connected in series with a detection cell, to which a substance interacting with a test substance binds; the thus connected cells are placed in a flow channel system; and a liquid is then fed through the reference cell and the detection cell, thereby measuring the change in the surface plasmon resonance.

Moreover, in the present invention, the ratio (Ve/Vs) of the amount of a liquid exchanged for a single measurement (Ve ml) to the volume of a cell used for measurement (Vs ml) (meaning the total volume of cells when the aforementioned reference cell and detection cell are both used) is set between 1 and 100, for example. Such Ve/Vs is more preferably between 1 and 50, and particularly preferably between 1 and 20. The volume of a cell used for measurement (Vs ml) is not particularly limited. It is preferably between 1×10$^{-6}$ and 1.0 ml, and particularly preferably between 1×10$^{-5}$ and 1×10$^{-1}$ ml. The time required for the exchange of the liquid is preferably between 0.01 second and 100 seconds, and more preferably between 0.1 second and 10 seconds.

The surface plasmon resonance phenomenon occurs due to the fact that the intensity of monochromatic light reflected from the border between an optically transparent substance such as glass and a metal thin film layer depends on the refractive index of a sample located on the outgoing side of the metal. Accordingly, the sample can be analyzed by measuring the intensity of reflected monochromatic light. The surface plasmon resonance measurement device used in the present invention will be described below.

The surface plasmon resonance measurement device is a device for analyzing the properties of a substance to be measured using a phenomenon whereby a surface plasmon is excited with a lightwave. One example of the surface plasmon resonance measurement device used in the present invention comprises a dielectric block, a metal film formed on a face of the dielectric block, a light source for generating a light beam, an optical system for allowing the above light beam to enter the above dielectric block such that total reflection conditions can be obtained at the interface between the above dielectric block and the above metal film and that components at various incident angles can be contained, and a light-detecting means for detecting the state of surface plasmon resonance by measuring the intensity of the light beam totally reflected at the above interface.

Moreover, as stated above, the above dielectric block is formed as one block comprising the entity of the entrance face and exit face of the above light beam and a face on which the above metal film is formed, and the above metal film is integrated with this dielectric block.

In the present invention, more specifically, a surface plasmon resonance measurement device shown in FIGS. 1 to 32 of Japanese Patent Laid-Open No. 2001-330560, and a surface plasmon resonance device shown in FIGS. 1 to 15 of Japanese Patent Laid-Open No. 2002-296177, can be preferably used. All of the contents as disclosed in Japanese Patent Laid-Open Nos. 2001-330560 and 2002-296177 cited in the present specification are incorporated herein by reference as a part of the disclosure of this specification.

For example, the surface plasmon resonance measurement device described in Japanese Patent Laid-Open No. 2001-330560 is characterized in that it comprises: a dielectric block; a thin metal film formed on a face of the dielectric block; multiple measurement units comprising a sample-retaining mechanism for retaining a sample on the surface of the thin film; a supporting medium for supporting the multiple measurement units; a light source for generating a light beam; an optical system for allowing the above light beam to enter the dielectric block at various angles so that total reflection conditions can be obtained at the interface between the dielectric block and the metal film; a light-detecting means for measuring the intensity of the light beam totally reflected at the above interface and detecting the state of attenuated total reflection caused by surface plasmon resonance; and a driving means for making the above supporting medium, the above optical system and the above light-detecting means move relative to one another, and successively placing each of the above multiple measurement units in a certain position appropriate to the above optical system and the above light-detecting means, so that the above total reflection conditions and various incident angles can be obtained with respect to each dielectric block of the above multiple measurement units.

It is to be noted that in the above measurement device, the above optical system and light-detecting means are kept in a resting state and the above driving means makes the above supporting medium move.

In such a case, the above supporting medium is desirably a turntable for supporting the above multiple measurement units on a circle centered on a rotation axis, and the above driving means is desirably a means for intermittently rotating this turntable. In this case, a medium for supporting the above multiple measurement units that are linearly arranged in a line may be used as the above supporting medium, and a means that makes such a supporting medium move linearly in an intermittent fashion in the direction in which the above multiple measurement units are arranged may be applied as the above driving means.

Otherwise, on the contrary, it may also be possible that the above supporting medium be retained in a resting state and that the above driving means makes the above optical system and light-detecting means move.

In such a case, the above supporting medium is desirably a medium for supporting the above multiple measurement units on a circle, and the above driving means is desirably a means for intermittently rotating the above optical system and light-detecting means along the multiple measurement units supported by the above supporting medium. In this case, a medium for supporting the above multiple measurement units that are linearly arranged. in a line may be used as the above supporting medium, and a means that makes the above optical system and light-detecting means move linearly in an intermittent fashion along the multiple measurement units supported by the above supporting medium may be applied as the above driving means.

Otherwise, when the above driving means has a rolling bearing that supports a rotation axis, the driving means is desirably configured such that after the rotation axis has been rotated to a certain direction and a series of measurements for the above multiple measurement units has been terminated, the above rotation axis is equivalently rotated to the opposite direction, and then it is rotated again to the same above direction for the next series of measurements.

In addition, the above-described measurement device is desirably configured such that the above multiple measurement units are connected in a line with a connecting member so as to constitute a unit connected body and that the above supporting medium supports the unit connected body.

Moreover, in the above-described measurement device, it is desirable to establish a means for automatically feeding a given sample to each sample-retaining mechanism of the multiple measurement units supported by the above supporting medium.

Furthermore, in the above-described measurement device, it is desirable that the dielectric block of the above measurement unit be immobilized to the above supporting medium, that a thin film layer and a sample-retaining mechanism of the measurement unit be unified so as to constitute a measurement chip, and that the measurement chip be formed such that it is exchangeable with respect to the above dielectric block.

When such a measurement chip is applied, it is desirable to establish a cassette for accommodating a multiple number of the measurement chips and a chip-supplying means for successively taking a measurement chip out of the cassette and supplying it in a state in which it is connected to the above dielectric block.

Otherwise, it may also be possible to unify the dielectric block of the measurement unit, the thin film layer and the sample-retaining mechanism, so as to constitute a measurement chip, and it may also be possible for this measurement chip to be formed such that it is exchangeable with respect to the above supporting medium.

When a measurement chip has such a structure, it is desirable to establish a cassette for accommodating a multiple number of measurement chips and a chip-supplying means for successively taking a measurement chip out of the cassette and supplying it in a state in which it is supported by the supporting medium.

The above optical system is desirably configured such that it makes a light beam enter the dielectric block in a state of convergent light or divergent light. Moreover, the above light-detecting means is desirably configured such that it detects the position of a dark line generated due to attenuated total reflection, which exists in the totally reflected light beam.

Furthermore, the above optical system is desirably configured such that it makes a light beam enter the above interface in a defocused state. In this case, the beam diameter of the light beam at the above interface in a direction wherein the above supporting medium moves is desirably ten times or greater the mechanical positioning precision of the above supporting medium.

Still further, the above-described measurement device is desirably configured such that the measurement unit is supported on the upper side of the above supporting medium, such that the above light source is placed so as to project the above light beam from a position above the above supporting medium to downwards, and such that the above optical system comprises a reflecting member for reflecting upwards the above light beam projected to downwards as described above and making it proceed towards the above interface.

Still further, the above-described measurement device is desirably configured such that the above measurement unit is supported on the upper side of the above supporting medium, such that the above optical system is constituted so as to make the above light beam enter the above interface from the downside thereof, and such that the above light-detecting means is placed in a position above the above supporting medium with a light-detecting plane thereof facing downwards, as well as comprising a reflecting member for reflecting upwards the totally reflected light beam at the above interface and making it proceed towards the above light-detecting means.

What is more, the above-described measurement device desirably comprises a temperature-controlling means for maintaining the temperature of the above measurement unit before and/or after being supported by the above supporting medium at a predetermined temperature.

Moreover, the above-described measurement device desirably comprises a means for stirring the sample stored in the sample-retaining mechanism of the measurement unit supported by the above supporting medium before detecting the state of attenuated total reflection as mentioned above.

Furthermore, in the above-described measurement device, it is desirable to establish in at least one of the multiple measurement units supported by the above supporting medium a standard solution-supplying means for supplying a standard solution having optical properties associated with the optical properties of the above sample, as well as a correcting means for correcting data regarding the above attenuated total reflection state of the sample based on the data regarding the above attenuated total reflection state of the above standard solution.

In such a case, if the sample is obtained by dissolving a test substance in a solvent, it is desirable that the above standard solution-supplying means be a means for supplying the above solvent as a standard solution.

Still further, the above measurement device desirably comprises: a mark for indicating individual recognition information; a reading means for reading the above mark from the measurement unit used in measurement; an inputting means for inputting sample information regarding the sample supplied to the measurement unit; a displaying means for displaying measurement results; and a controlling means connected to the above displaying means, inputting means and reading means, which stores the above individual recognition information and sample information of each measurement unit while associating them with each other, as well as making the above displaying means display the measurement results of the sample retained in a certain measurement unit while associating them with the above individual recognition information and sample information of each measurement unit.

When a substance interacting with a physiologically active substance is detected or measured using the above-described measurement device, a state of attenuated total reflection is detected in a sample contained in one of the above measurement units, and thereafter, the above supporting medium, optical system and light-detecting means are moved relative to one another, so that a state of attenuated total reflection is detected in a sample contained in another measurement unit. Thereafter, the above supporting medium, optical system and light-detecting means are again moved relative to one another, so that a state of attenuated total reflection is detected again the sample contained in the above one measurement unit, thereby completing the measurement.

The measurement chip used in the present invention is used for the surface plasmon resonance measurement device having a structure described herein, and comprises a dielectric block and a metal film formed on a face of the dielectric block, in which the dielectric block is formed as one block comprising the entirety of the entrance face and exit face of the light beam and a face on which the above metal film is formed, the above metal film is integrated with the above dielectric block.

A metal constituting the metal film is not particularly limited, as long as surface plasmon resonance is generated. Examples of a preferred metal may include free-electron metals such as gold, silver, copper, aluminum or platinum. Of these, gold is particularly preferable. These metals can be used singly or in combination. Moreover, considering adherability to the above substrate, an interstitial layer consisting of chrome or the like may be provided between the substrate and a metal layer.

The film thickness of a metal film is not limited. When the metal film is used for a surface plasmon resonance biosensor, the thickness is preferably between 0.1 nm and 500 nm, and particularly preferably between 1 nm and 200 nm. If the thickness exceeds 500 nm, the surface plasmon phenomenon of a medium cannot be sufficiently detected. Moreover, when an interstitial layer consisting of chrome or the like is provided, the thickness of the interstitial layer is preferably between 0.1 nm and 10 nm.

Formation of a metal film may be carried out by common methods, and examples of such a method may include sputtering method, evaporation method, ion plating method, electroplating method, and nonelectrolytic plating method.

A metal film is preferably placed on a substrate. The description "placed on a substrate" is used herein to mean a case where a metal film is placed on a substrate such that it directly comes into contact with the substrate, as well as a case where a metal film is placed via another layer without directly coming into contact with the substrate. When a substrate used in the present invention is used for a surface plasmon resonance biosensor, examples of such a substrate may include, generally, optical glasses such as BK7, and synthetic resins. More specifically, materials transparent to laser beams, such as polymethyl methacrylate, polyethylene terephthalate, polycarbonate or a cycloolefin polymer, can be used. For such a substrate, materials that are not anisotropic with regard to polarized light and having excellent workability are preferably used.

Preferably, the metal film has a functional group capable of immobilizing a physiologically active substance (namely, a ligand to a test substance) on the outermost surface of the substrate. The term "the outermost surface of the substrate" is used to mean "the surface, which is farthest from the substrate".

Examples of a preferred functional group may include —OH, —SH, —COOH, —NR$^1$R$^2$ (wherein each of R$^1$ and R$^2$ independently represents a hydrogen atom or lower alkyl group), —CHO, —NR$^3$NR$^1$R$^2$ (wherein each of R$^1$, R$^2$ and R$^3$ independently represents a hydrogen atom or lower alkyl group), —NCO, —NCS, an epoxy group, and a vinyl group. The number of carbon atoms contained in the lower alkyl group is not particularly limited herein. However, it is generally about C1 to C10, and preferably C1 to C6.

Examples of the method of introducing such a functional group include a method which involves applying a polymer containing a precursor of such a functional group on a metal surface or metal film, and then generating the functional group from the precursor located on the outermost surface by chemical treatment.

In the measurement chip obtained as mentioned above, a physiologically active substance is covalently bound thereto via the above functional group, so that the physiologically active substance can be immobilized on the metal film.

A physiologically active substance immobilized on the surface for the measurment chip of the present invention is not particularly limited, as long as it interacts with a measurement target. Examples of such a substance may include an immune protein, an enzyme, a microorganism, nucleic acid, a low molecular weight organic compound, a nonimmune protein, an immunoglobulin-binding protein, a sugar-binding protein, a sugar chain recognizing sugar, fatty acid or fatty acid ester, and polypeptide or oligopeptide having a ligand-binding ability.

Examples of an immune protein may include an antibody whose antigen is a measurement target, and a hapten. Examples of such an antibody may include various immunoglobulins such as IgG, IgM, IgA, IgE or IgD. More specifically, when a measurement target is human serum albumin, an anti-human serum albumin antibody can be used as an antibody. When an antigen is an agricultural chemical, pesticide, methicillin-resistant *Staphylococcus aureus*, antibiotic, narcotic drug, cocaine, heroin, crack or the like, there can be used, for example, an anti-atrazine antibody, anti-kanamycin antibody, anti-metamphetamine antibody, or antibodies against O antigens 26, 86, 55, 111 and 157 among enteropathogenic *Escherichia coli*.

An enzyme used as a physiologically active substance herein is not particularly limited, as long as it exhibits an activity to a measurement target or substance metabolized from the measurement target. Various enzymes such as oxidoreductase, hydrolase, isomerase, lyase or synthetase can be used. More specifically, when a measurement target is glucose, glucose oxidase is used, and when a measurement target is cholesterol, cholesterol oxidase is used. Moreover, when a measurement target is an agricultural chemical, pesticide, methicillin-resistant *Staphylococcus aureus*, antibiotic, narcotic drug, cocaine, heroin, crack or the like, enzymes such as acetylcholine esterase, catecholamine esterase, noradrenalin esterase or dopamine esterase, which show a specific reaction with a substance metabolized from the above measurement target, can be used.

A microorganism used as a physiologically active substance herein is not particularly limited, and various microorganisms such as *Escherichia coli* can be used.

As nucleic acid, those complementarily hybridizing with nucleic acid as a measurement target can be used. Either DNA (including cDNA) or RNA can be used as nucleic acid. The type of DNA is not particularly limited, and any of native DNA, recombinant DNA produced by gene recombination and chemically synthesized DNA may be used.

As a low molecular weight organic compound, any given compound that can be synthesized by a common method of synthesizing an organic compound can be used.

A nonimmune protein used herein is not particularly limited, and examples of such a nonimmune protein may include avidin (streptoavidin), biotin, and a receptor.

Examples of an immunoglobulin-binding protein used herein may include protein A, protein G, and a rheumatoid factor (RF).

As a sugar-binding protein, for example, lectin is used.

Examples of fatty acid or fatty acid ester may include stearic acid, arachidic acid, behenic acid, ethyl stearate, ethyl arachidate, and ethyl behenate.

When a physiologically active substance is a protein such as an antibody or enzyme, or nucleic acid, an amino group, thiol group or the like of the physiologically active substance is covalently bound to a functional group located on a metal surface, so that the physiologically active substance can be immobilized on the metal surface.

A measurement chip to which a physiologically active substance is immobilized as described above can be used to detect and/or measure a substance which interacts with the physiologically active substance.

The present invention is described in detail by the following examples, but the scope of the present invention is not limited by these examples.

EXAMPLES (1) Immobilization of Physiologically Active Substance on Sensor Surface A commercially available CM5 chip (manufactured by Biacore) was established on the cartridge block of a commercially available surface plasmon resonance biosensor (BIACORE 3000; manufactured by Biacore). Thereafter, 300 μl of a mixed solution of 1-ethyl-2,3-dimethylaminopropylcarbodiimide (400 mm) and N-hydroxysuccinimide (100 mm) was passed through a measurement cell thereof at a flow rate of 10 μl/min for 10 minutes. Thereafter, it was washed with a buffer (10 mm HEPES (N-2-hydroxyethylpiperazin-N'-2-ethanesulfonic acid), 150 mm NaCl, and 10 mm $CaCl_2$). Subsequently, a protein A solution (prepared by dissolving protein A in a buffer to a concentration of 1 mg/ml) was replaced for only flow channels 2 and 3, and it was passed through them for 30 minutes, so that protein A was immobilized thereon. Thereafter, 1 M ethanolamine solution was passed through all the flow channels for 10 minutes, followed by washing with a buffer for 10 minutes. Thus, protein A was immobilized on the sensor surface.

(2) Analysis of IgG Adsorption

A solution containing 10 μg/ml anti-BSA mouse IgG (molecular weight: 150,000) was passed through all the flow channels on the sensor surface produced in (1) above at a flow rate of 20 μl/min, and SPR signals were measured. The difference between the mean value of flow channels 2 and 3 and the mean value of flow channels 1 and 4 was defined as a binding signal. The measurement results were analyzed with software included with BIAcore 3000, so as to obtain Rmax=880 RU, ka=$1.4 \times 10^5$ $M^{-1} \cdot s^{-1}$, and kd=$5.6 \times 10^{-4}$ $s^{-1}$.

(3) Analysis of BSA Adsorption

A solution of 4.4 μg/ml BSA (molecular weight: 66,200) was passed through all the flow channels on the sensor surface produced in (1) above at a flow rate of 20 μl/min, and SPR signals were measured. The difference between the mean value of flow channels 2 and 3 and the mean value of flow channels 1 and 4 was defined as a binding signal. The measurement results were calculated by the nonlinear regression method using Rmax=880 RU, so as to obtain ka=$8.8 \times 10^5$ $M^{-1} \cdot s^{-1}$, and kd=$1.1 \times 10^{-1}$ $s^{-1}$.

(4) Calculation of Adsorption of IgG-BSA Mixture

Figure 2:
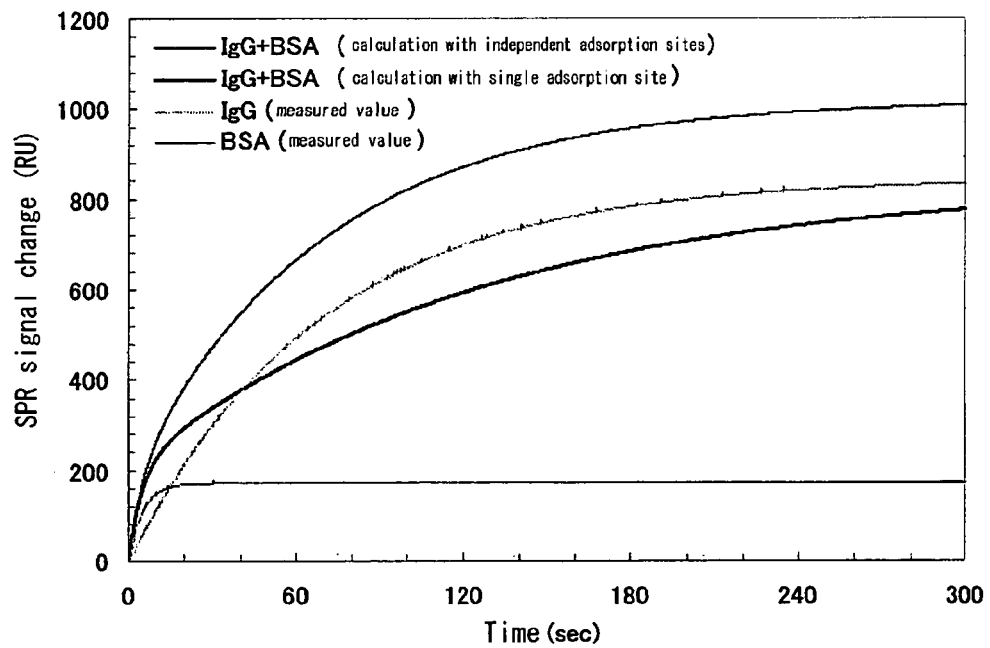
FIG. 2 is a view showing the results obtained by calculating a change in SPR signals obtained when IgG and BSA are simultaneously adsorbed, using ka and kd obtained by the adsorption analysis of IgG and that of BSA.

From the results obtained in (2) and (3) above, the change in the SPR signals obtained when 10 μg/ml anti-BSA mouse IgG and 4.4 μg/ml BSA were simultaneously adsorbed was calculated. The results are shown in FIG. 2.

Figure 3:
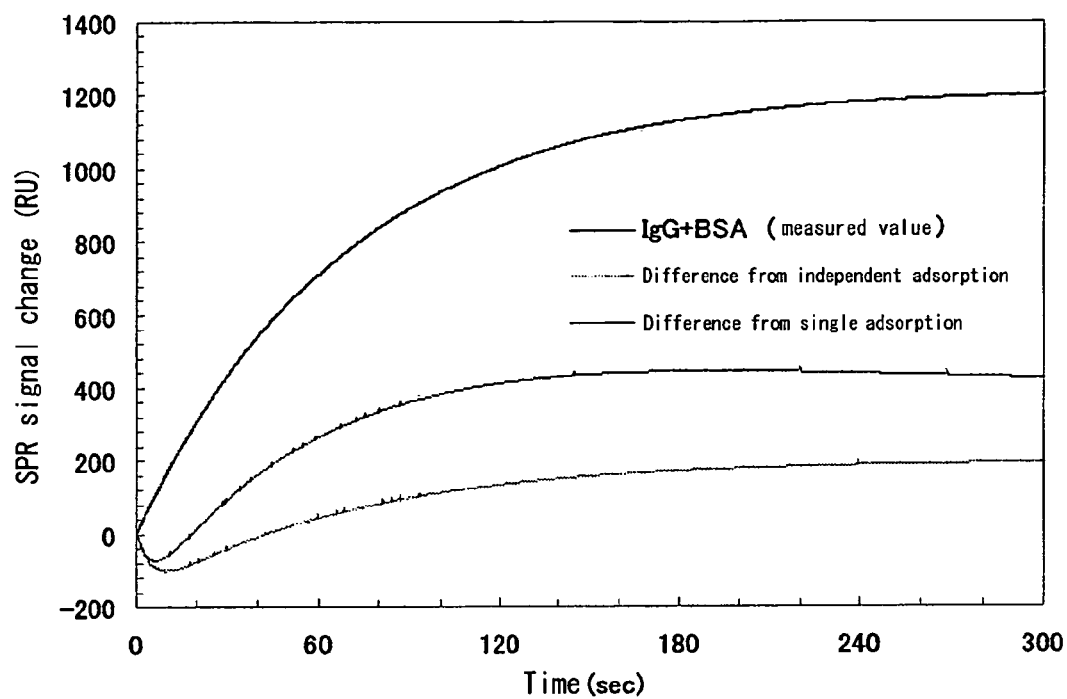
FIG. 3 is a view showing the difference between the measurement value of a mixture consisting of IgG and BSA and a predicted calculation value thereof.

(5) Display of Difference Between Measurement Value of IgG-BSA Mixture and Estimated Calculation Value A solution of 4.4 μg/ml BSA (molecular weight: 66,200) and 10 μg/ml anti-BSA mouse IgG (molecular weight: 150,000) was passed through all the flow channels on the sensor surface produced in (1) above at a flow rate of 20 μl/min, and SPR signals were measured. The difference between the mean value of flow channels 2 and 3 and the mean value of flow channels 1 and 4 was defined as a binding signal. The difference between the actually measured value and the calculation result obtained in (4) above is shown in FIG. 3. The results clearly show that the adsorption site is neither independent adsorption sites, nor a single adsorption site.

EFFECTS OF THE INVENTION

According to the present invention, by analyzing a phenomenon whereby multiple test substances are simultaneously adsorbed to a ligand, such test substances can be analyzed. In addition, according to the present invention, it becomes possible to rapidly screen many types of test substances by differentiating competitive adsorption of test substances to a ligand from the change in the adsorption site itself due to adsorption of substances to a ligand.

The invention claimed is:

1. A method for analyzing the interaction of test substances with a ligand by measuring the change in the surface plasmon resonance using a surface plasmon resonance measurement device which comprises
   a) a metal film,
   b) a light source for generating a light beam, an optical system for allowing such a light beam to enter the interface of the metal film so that total reflection conditions can be obtained at the interface thereof and so that various incidence angles can be included,
   c) a flow channel system comprising a cell formed on the above metal film, and
   d) a light-detecting means for detecting the state of surface plasmon resonance by measuring the intensity of the light beam totally reflected at the above interface;
   wherein the above-described method comprises:
   1. supplying a solution containing two or more types of test substances after supplying a solution containing no test substances;
   2. measuring the change in the surface plasmon resonance;
   3. analyzing the difference between the change in the surface plasmon resonance that is predicted from the adsorption rate constant (ka) and dissociation rate constant (kd) of each of the test substances that had previously been measured and the change in the surface plasmon resonance that has actually been measured; and
   4. identifying the change in the adsorption site due to adsorption of the test substances to a ligand by the above step 3 to analyze the interaction of test substances with a ligand.

2. The method of claim 1 which comprises displaying the difference between the change in the surface plasmon resonance that is predicted from the adsorption rate constant (ka) and dissociation rate constant (kd) of each of the test substances that had previously been measured and the change in the surface plasmon resonance that has actually been measured, in the form of data.

3. The method of claim 1 wherein the change in the surface plasmon resonance is measured in a state where the flow of the liquid has then been terminated after the liquid in the above-described flow channel system has been exchanged so that a solution containing no test substances is replaced with a solution containing two or more types of test substances.

4. The method of claim 1 wherein the difference between the change in the surface plasmon resonance that is predicted from the adsorption rate constant (ka) and dissociation rate constant (kd) of each of the test substances that had previously been measured and the change in the surface plasmon resonance that has actually been measured as described above is analyzed, and a test substance causing the change in the binding site due to the binding of the test substance to a ligand is identified based on the presence of the above-mentioned difference.

5. The method of claim 1 wherein the change in the surface plasmon resonance that is predicted from the adsorption rate constant (Ka) and dissociation rate constant (kd) of each of the test substances that had previously been measured is determined from the formulas (2) and (3):

$$\frac{dR}{dt} = A \cdot \sum_{i=1}^{n} \left( Ka_i \cdot Cs_i \cdot \left(1 - \sum_{i=1}^{n} \theta_i \right) - kd_i \cdot \theta_i \right) \cdot MW_i \quad \text{Formula (2)}$$

wherein, in the formula (2), A represents a constant used for conversion from the adsorbed weight to SPR signals, and $MW_i$, $Cs_i$, $\theta_i$, $Ka_i$, and $Kd_i$ represent the molecular weight of compound i, the concentration thereof, the adsorption site share thereof, and adsorption rate constant, and a dissociation rate constant, respectively, $$\frac{dR}{dt} = \sum_{i=1}^{n} \left( Ka_i \cdot Cs_i \cdot \left( R\max_i - \sum_{i=1}^{n} R_i \right) - kd_i \cdot R_i \right) \quad \text{Formula (3)}$$

wherein, in the formula (3), $R_i$ represents a change in SPR signals of compound i; and $R\max_i$ represents the maximum adsorbed SPR signals of compound i.

* * * * *